(12) United States Patent
Hodde et al.

(10) Patent No.: US 8,741,352 B2
(45) Date of Patent: Jun. 3, 2014

(54) GRAFT MATERIALS CONTAINING ECM COMPONENTS, AND METHODS FOR THEIR MANUFACTURE

(75) Inventors: Jason P. Hodde, West Lafayette, IN (US); David M. J. Ernst, Indianapolis, IN (US); Lal Ninan, Santa Rosa, CA (US); Sherry Voytik-Harbin, Zionsville, IN (US); Nathan Hammond, Somerville, MA (US)

(73) Assignee: Cook Biotech Incorporated, West Lafayette, IN (US)

( * ) Notice: Subject to any disclaimer, the term of this patent is extended or adjusted under 35 U.S.C. 154(b) by 1102 days.

(21) Appl. No.: 11/851,923

(22) Filed: Sep. 7, 2007

(65) Prior Publication Data

US 2008/0107750 A1 May 8, 2008

Related U.S. Application Data

(63) Continuation of application No. 11/650,647, filed on Jan. 8, 2007, now abandoned, which is a continuation of application No. 11/435,393, filed on May 16, 2006, now abandoned, and a continuation-in-part of application No. 10/569,218, filed as application No. PCT/US2004/027557 on Dec. 18, 2006, now Pat. No. 8,021,692.

(60) Provisional application No. 60/497,746, filed on Aug. 25, 2003, provisional application No. 60/681,522, filed on May 16, 2005, provisional application No. 60/681,278, filed on May 16, 2005, provisional application No. 60/681,689, filed on May 16, 2005, provisional application No. 60/681,511, filed on May 16, 2005.

(51) Int. Cl.
| | | |
|---|---|---|
| *A61K 35/12* | (2006.01) | |
| *A61L 27/36* | (2006.01) | |
| *A61L 27/22* | (2006.01) | |
| *A61K 35/38* | (2006.01) | |
| *A61K 38/18* | (2006.01) | |
| *A61K 35/37* | (2006.01) | |

(52) U.S. Cl.
CPC ............. *A61K 35/37* (2013.01); *A61L 27/3629* (2013.01); *A61L 27/3633* (2013.01); *A61L 27/3687* (2013.01); *A61L 27/227* (2013.01); *A61K 35/38* (2013.01); *A61K 38/1825* (2013.01)
USPC .................................. 424/520; 422/28; 422/1

(58) Field of Classification Search
None
See application file for complete search history.

(56) References Cited

U.S. PATENT DOCUMENTS

| | | | |
|---|---|---|---|
| 5,275,826 A | 1/1994 | Badylak et al. | |
| 6,206,931 B1 * | 3/2001 | Cook et al. ................. | 623/23.75 |
| 6,264,992 B1 * | 7/2001 | Voytik-Harbin et al. ..... | 424/551 |
| 6,444,229 B2 | 9/2002 | Voytik-Harbin et al. | |
| 2004/0078076 A1 | 4/2004 | Badylak et al. | |
| 2006/0235511 A1 | 10/2006 | Osborne | |

OTHER PUBLICATIONS

Lindberg, K; Badylak, S.F. Porcine small intestinal submucosa (SIS): a bioscaffold supporting in vitro primary human epidermal cell differentiation and synthesis of basement membrane proteins. Burns 27 (2001), 254-266.
Voytik-Harbin et al "Identification of Extractable Growth Factors From Small Intestine Submucosa," J Cell. Biochem. 67: 478-491 (1997).

* cited by examiner

*Primary Examiner* — Suzanne Ziska
(74) *Attorney, Agent, or Firm* — Woodard, Emhardt, Moriarty, McNett & Henry LLP

(57) ABSTRACT

Described are packaged, sterile medical graft products containing controlled levels of a growth factor such as Fibroblast Growth Factor-2 (FGF-2). Also described are methods of manufacturing medical graft products wherein processing, including sterilization, is controlled and monitored to provide medical graft products having modulated, known levels of a extracellular matrix factor, such as a growth factor, e.g. FGF-2. Preferred graft materials are extracellular matrix materials isolated from human or animal donors, particularly submucosa-containing extracellular matrix materials. Further described are ECM compositions that are or are useful for preparing gels, and related methods for preparation and use.

14 Claims, No Drawings

US 8,741,352 B2

GRAFT MATERIALS CONTAINING ECM COMPONENTS, AND METHODS FOR THEIR MANUFACTURE

REFERENCE TO RELATED APPLICATIONS

This application is a continuation application of U.S. patent application Ser. No. 11/650,647 filed Jan. 8, 2007, which is a continuation of U.S. patent application Ser. No. 11/435,393 filed May 16, 2006, which is a continuation-in-part of U.S. patent application Ser. No. 10/569,218, which is a National Stage of International Application No. PCT/US2004/027557 filed Aug. 25, 2004, which claims the benefit of U.S. Patent Application Ser. No. 60/497,746 filed Aug. 25, 2003, each of which is hereby incorporated by reference in its entirety. This application also claims the benefit of priority of U.S. Provisional Patent Application Ser. Nos. 60/681,522, 60/681,278, 60/681,689 and 60/681,511, all filed May 16, 2005, each of which is hereby incorporated by reference in its entirety.

BACKGROUND OF THE INVENTION

The present invention relates generally to materials useful for tissue grafting, and in particular to such materials derived from extracellular matrices and retaining both collagen and substances such as growth factors that contribute to the beneficial properties of the materials. In one aspect, the invention relates to extracellular matrix tissue graft materials containing one or more growth factors modulated to a predetermined level, and related methods of manufacturing.

Extracellular matrix (ECM) materials, including those derived from submucosa and other tissues, are known tissue graft materials. See, e.g., U.S. Pat. Nos. 4,902,508, 4,956, 178, 5,281,422, 5,372,821, 5,554,389, 6,099,567, and 6,206, 931. Tissues from various biological structures can be used for these purposes, including for example small intestine, stomach, the urinary bladder, skin, pericardium, dura mater, fascia, and the like. These sources provide collagenous materials useful in a variety of surgical procedures where tissue support and/or ingrowth are desired.

Submucosa and other ECM materials have been shown to include a variety of components other than collagen that that can contribute to the bioactivity of the materials and to their value in medical grafting and other uses. As examples, ECM materials can include growth factors, cell adhesion proteins, and proteoglycans. However, ECM materials are typically subjected to a battery of manipulations in the manufacture of finished products containing them. This presents challenges in obtaining finished products that not only possess the necessary physical properties and appropriate levels of biocompatibility and sterility, but also the desired bioactivity. The present invention is addressed to these needs.

SUMMARY

Accordingly, in one aspect, the present invention provides a method for manufacturing a tissue graft material such as a collagenous extracellular matrix containing at least one extractable, bioactive growth factor or other non-collagenous protein material, particularly Fibroblast Growth Factor-2 (FGF-2), at a predetermined amount. The method includes the steps of providing a non-sterile extracellular matrix material; fashioning a plurality of graft products from the extracellular matrix material; packaging the products; subjecting the packaged products to a sterilization procedure that affects the level of extractable bioactive growth factor (FGF-2) or other non-collagenous protein material in the products; and, taking and testing sample products of the sterilized packaged products to determine a level of a growth factor (FGF-2) in the sample products, wherein said determined level is representative of an approximate level of said growth factor in other ones of said products from the lot from which the sample product was taken.

In another aspect, the present invention provides a medical product that comprises a packaged, sterile animal-derived extracellular matrix material comprising FGF-2 at a level of at least about 50 nanograms per gram dry weight. Particularly preferred materials are lyophilized and/or include submucosa.

Another aspect of the invention provides a packaged, sterile extracellular matrix material isolated from animal tissue and including components native to the tissue, the matrix material including collagen, growth factors, proteoglycans, glycosaminoglycans, and having extractable, bioactive FGF-2 at a level of at least about 50 nanograms per gram dry weight.

Another aspect of the invention provides a method for manufacturing a sterile, extracellular matrix material. The method includes isolating an extracellular matrix material from animal tissue, the isolated extracellular matrix material including extractable FGF-2 at a first level; and, sterilizing the isolated extracellular matrix material under conditions to retain the extractable, bioactive FGF-2 in at least 10% of the first level.

Another aspect of the invention provides a method for manufacturing medical products. The method includes providing extracellular matrix material in non-sterile condition and isolated from animal tissue, the extracellular matrix material comprising extractable, bioactive FGF-2; packaging and sterilizing the extracellular matrix material to provide product lots each containing multiple, packaged extracellular matrix material products; taking sample products from the product lots; and testing the sample products to determine whether they include extractable, bioactive FGF-2 at a level above a predetermined level, e.g. above about 50 nanograms per gram dry weight.

Another aspect of the invention provides a medical product adapted for treating wounds, the product including an extracellular matrix material isolated from animal tissue, the material including bioactive components useful to treat wounds including but not limited to FGF-2. The FGF-2 is present in the extracellular matrix material at a level of at least about 50 nanograms per gram dry weight.

Another aspect of the invention relates to a medical product comprising a dry collagenous powder comprising extracellular matrix material, wherein the dry collagenous powder is effective to gel upon rehydration with an aqueous medium and comprises FGF-2 at a level of at least about 50 ng/g dry weight.

In another aspect, the invention relates to a medical product comprising a fluid composition comprising solubilized or suspended collagenous extracellular matrix material, wherein the fluid composition comprises FGF-2 at a level of about 0.1 ng/ml to about 100 ng/ml.

In another embodiment, the invention provides a method for disinfecting an aqueous extracellular matrix hydrolysate composition. The aqueous extracellular matrix hydrolysate composition is contacted with an oxidizing disinfectant for a period of time and under conditions sufficient to disinfect the aqueous extracellular matrix hydrolysate composition.

Another aspect of the invention relates to a method for preparing a disinfected, extracellular matrix hydrolysate composition. This method comprises forming an aqueous extracellular matrix hydrolysate. A first dialysis step is conducted and includes dialyzing the aqueous extracellular matrix hydrolysate against an aqueous medium containing an oxidizing disinfectant so as to contact and disinfect the extracellular matrix hydrolysate with the oxidizing disinfectant and thereby form a disinfected extracellular matrix hydrolysate. A second dialysis step includes dialyzing the disinfected extracellular matrix hydrolysate under conditions to remove the oxidizing disinfectant.

In another embodiment, the invention provides an extracellular matrix hydrolysate product having extracellular matrix components disinfected by contact of an aqueous medium containing the extracellular matrix hydrolysate with an oxidizing disinfectant. The extracellular matrix hydrolysate product can take on a variety of forms, including a dry powdery material, a non-gelled aqueous composition, a gel, or a sponge.

Still another embodiment of the invention provides an extracellular matrix graft material that includes an extracellular matrix hydrolysate combined with extracellular matrix particles. In a preferred form, the graft material includes an aqueous medium having said extracellular matrix hydrolysate in a dissolved state with the extracellular matrix particles suspended therein, desirably wherein the medium exhibits gel-forming capacity.

Another embodiment of the invention provides an extracellular matrix graft material that includes a sterile, injectable fluid extracellular matrix composition including an aqueous medium containing an extracellular matrix hydrolysate. The extracellular matrix hydrolysate is present in the composition at a level of at least about 20 mg/ml, for example in the range of about 20 mg/ml to about 200 mg/ml.

Additional aspects as well as features and advantages of the invention will be apparent to those of ordinary skill in the art from the descriptions herein.

DETAILED DESCRIPTION

For the purposes of promoting an understanding of the principles of the invention, reference will now be made to certain embodiments and specific language will be used to describe the same. It will nevertheless be understood that no limitation of the scope of the invention is thereby intended, such alterations and further modifications in the illustrated device, and such further applications of the principles of the invention as described herein being contemplated as would normally occur to one skilled in the art to which the invention relates.

As disclosed above, in one aspect, the present invention provides packaged, sterile medical products including tissue grafts materials containing one or more growth factors, and methods for manufacturing the same. As for the tissue graft material used, it will desirably be a naturally-derived material such as an extracellular matrix (ECM) material. Preferred are naturally-derived collagenous ECMs isolated from suitable animal or human tissue sources. Suitable extracellular matrix materials include, for instance, submucosa (including for example small intestinal submucosa, stomach submucosa, urinary bladder submucosa, or uterine submucosa, each of these isolated from juvenile or adult animals), renal capsule membrane, amnion, dura mater, pericardium, serosa, peritoneum or basement membrane materials, including liver basement membrane or epithelial basement membrane materials. These materials may be isolated and used as intact natural sheet forms, or reconstituted collagen layers including collagen derived from these materials and/or other collagenous materials may be used. For additional information as to submucosa materials useful in the present invention, and their isolation and treatment, reference can be made to U.S. Pat. Nos. 4,902,508, 5,554,389, 5,993,844, 6,206,931, and 6,099,567. Renal capsule membrane can also be obtained from warm-blooded vertebrates, as described more particularly in International Patent Application serial No. PCT/US02/20499 filed Jun. 28, 2002, published Jan. 9, 2003, as WO03002165.

Preferred ECM base materials contain residual bioactive proteins or other ECM components derived from the tissue source of the materials. For example, they may contain Fibroblast Growth Factor-2 (basic FGF), Transforming Growth Factor-beta (TGF-beta) and vascular endothelial growth factor (VEGF). It is also expected that ECM base materials of the invention may contain additional bioactive components including, for example, one or more of glycosaminoglycans, glycoproteins, proteoglycans, and/or growth factors.

It has been discovered that the sterilization conditions utilized in the manufacture of tissue graft materials can significantly impact the level of one or more of such bioactive components or growth factors, including for example FGF-2. Accordingly, in accordance with the invention, sterilization protocols can be selected and controlled to modulate the level of growth factors, for example by either intentionally reducing growth factor levels to a predetermined level or below, or to retain at least a given percentage or level of one or more growth factors, particularly FGF-2, in the material. In certain embodiments of the invention, the ECM or other graft material is processed to finished, packaged, sterile products containing FGF-2 at a level of at least 50 ng/g dry weight, or even at least about 60, at least about 70, at least about 80, or at least about 100 ng/g dry weight. In other embodiments of the invention, an ECM material will have a first level of a bioactive component, such as FGF-2 or another growth factor, after isolation from the animal or human donor source tissue and rinsing with a rinse agent such as water. The ECM material will thereafter be processed under controlled conditions, including sterilization, to provide packaged, sterile medical products containing at least about 10% of said first level of the FGF-2 or other bioactive component, or even at least 15%, 20%, 30% or even 50% or more of said first level.

Illustratively, it has been found that sterilization protocols including ethylene oxide (EO) sterilization, electron beam (E-beam) radiation and gas plasma sterilization (e.g. Sterrad®) can significantly reduce levels of extractable, bioactive FGF-2. At the same time, these sterilization techniques have significantly lower or essentially no impact on levels of extractable, bioactive TGF-beta. Advantageously, the modulation of growth factors imparted by the sterilization technique can be used to affect and optimize levels of given growth factors, their ratios, etc., to prepare a graft material better suited for a particular medical indication wherein the retained growth factor or growth factors are beneficial to the indication, and/or wherein eliminated growth factor or growth factors are deleterious to the medical indication.

For example, FGF-2 is known to stimulate angiogenesis, neurite growth, plasminogen activator (PA) secretion, and matrix metalloproteinase 1 (MMP-1) production. Correspondingly, levels of FGF-2 can be retained and optimized for use in the graft material in wound healing (angiogenesis), treatment of nervous tissue (neurite outgrowth) including peripheral nervous tissue and central nervous tissue, modulating adhesion formation (by stimulating PA), and facilitating collagen turnover and degradation (by stimulating MMP-1 production). Thus, FGF-2 levels can be retained in the material as high as possible by selecting and optimizing the sterilization protocol. For instance, it has been found that non-sterile isolated submucosa layers (and in particular isolated from small intestine), contain relatively high levels of extractable, bioactive FGF-2. For example, submucosa tissue isolated from small intestine and minimally treated, e.g. only by rinsing, may be recovered so as to contain in excess of about 100 nanograms per gram of FGF-2 dry weight and potentially even higher levels such as above about 200 or about 400 nanograms per gram. In manufacturing, it may be beneficial to retain as much of this FGF-2 in the material as possible. Thus, intermediate steps between the isolation of the original submucosa material and the finished, packaged medical article, can be selected and controlled so as to maintain as much active FGF-2 in the material as possible.

As one example, an isolated, small intestinal submucosa material disinfected as described in U.S. Pat. No. 6,206,931 with peracetic acid may contain from about 70 to about 200 nanograms per gram (dry weight) of FGF-2. It has been found that sterilization treatments using ethylene oxide, E-beam, and gas plasma sterilization techniques significantly reduce the levels of FGF-2 in the disinfected material. Among these, E-beam sterilization had the smallest impact on FGF-2 levels, with E-beam sterilized submucosa having FGF-2 levels ranging from about 75 nanograms per gram dry weight to about 150 nanograms per gram dry weight, and generally retaining greater than about 50% of the FGF-2 level of the disinfected submucosa material. Gas plasma sterilized material had an FGF-2 level ranging from about 60 nanograms per gram dry weight to about 110 nanograms per gram dry weight, and retaining at least 40% of the FGF-2 level of the disinfected submucosa material. Thus, in embodiments of the invention, materials sterilized using E-beam or gas plasma techniques are used in products configured for and methods for treating patients where relatively high FGF-2 levels are beneficial, for example wound healing, treatment of tissue of the nervous system, modulating adhesions, or facilitating collagen turn-over and degradation.

On the other hand, ethylene oxide sterilization at both low temperature and high temperature conditions had a more significant impact in reducing the FGF-2 levels, with products typically having from about 10 to about 40 nanograms per gram of FGF-2 dry weight, and retaining less than about 40% of the FGF-2 level of the disinfected submucosa material (e.g. about 10% to about 40%). In this ethylene oxide work, the high temperature conditions tended to do have a slightly greater effect in reducing the FGF-2 levels than the low temperature conditions. Accordingly, in the ethylene oxide and potentially other sterilization techniques, the temperature may be increased or decreased to provide a respective higher or lower level of reduction of FGF-2 and/or other growth factors or non-collagenous ECM proteins. Similarly, the total dose of sterilant chemical or energy can be increased or decreased to provide a respective higher or lower level of reduction of FGF-2 and/or other growth factors or non-collagenous ECM proteins. Increased doses of sterilant can be achieved, for instance, through a longer, single exposure of the graft material to the sterilant, or through multiple, discreet exposures of the graft material to the sterilant.

In accordance with the invention, in addition to controlling the sterilization protocol, a number of other manufacturing techniques can be undertaken to provide a packaged, sterilized graft product with a controlled level of one or more growth factors, including for example FGF-2. As a first measure, where it is desired to retain as high as possible a level of FGF-2, the animal-derived collagenous ECM can be processed and preserved from the time of harvest to the time at which FGF-2 or other growth factor is protected against further significant degradation. For these purposes, the harvested tissue from which the ECM material is to be isolated may be placed soon or immediately after harvest in a stabilizing solution that prevents degradation of the product including for example, osmotic, hypoxic, autolytic, and/or proteolytic degradation. This solution can also protect against bacterial contamination. To achieve these effects, the stabilizing material may be a buffered solution of anti-oxidants, antibiotics, protease inhibitors, oncotic agents, or other stabilizing agents.

Illustratively, enzymes (e.g. superoxide dismutase and catalase) may be used to neutralize the superoxide anion and hydrogen peroxide or compounds that can directly react with and neutralize other free-radical species. Antioxidants may be added and include tertiary butylhydroquinone (BHT), alpha tocopherol, mannitol, hydroxyurea, glutathione, ascorbate, ethylenediaminetetraacetic acid (EDTA) and the amino acids histidine, proline and cysteine. In addition to antioxidants, the stabilizing solution may contain agents to inhibit hypoxic alteration to normal biochemical pathways, for example, allopurinol to inhibit xanthine dehydrogenase, lipoxigenase inhibitors, calcium channel blocking drugs, calcium binding agents, iron binding agents, metabolic intermediaries and substrates of adenosine triphosphate (ATP) generation.

The stabilizing solution may also contain one or more antibiotics, antifungal agents, protease inhibitors, proteoglycans, and an appropriate buffer. Antibiotics can be used to inhibit or prevent bacterial growth and subsequent tissue infection. Antibiotics may be selected from the group of penicillin, streptomycin, gentamicin, kanamycin, neomycin, bacitracin, and vancomycin. Additionally, anti-fungal agents may be employed, including amphotericin-B, nystatin and polymyxin.

Protease inhibitors may be included in the stabilizing solution to inhibit endogenous proteolytic enzymes which, when released, can cause irreversible degradation of the ECM, as well as the release of chemoattractant factors. These chemoattractants solicit the involvement of polymorphonuclear leukocytes, macrophages and other natural killer cells which generate a nonspecific immune response that can further damage the ECM. Protease inhibitors can be selected from the group consisting of N-ethylmaleimide (NEM), phenylmethylsulfonyl fluoride (PMSF), ethylenediaminetetraacetic acid (EDTA), ethylene glycol-bis(2-aminoethyl ether)-N,N,N',N'-tetraacetic acid (EGTA), leupeptin, ammonium chloride, elevated pH and apoprotinin.

Glycosaminoglycans may be included in the stabilizing solution to provide a colloid osmotic balance between the solution and the tissue, thereby preventing the diffusion of endogenous glycosaminoglycans from the tissue to the solution. Endogenous glycosaminoglycans serve a variety of functions in collagen-based connective tissue physiology. They may be involved in the regulation of cell growth and differentiation (e.g. heparin sulfate and smooth muscle cells) or, alternatively, they are important in preventing pathological calcification (as with heart valves). Glycosaminoglycans are also involved in the complex regulation of collagen and elastin synthesis and remodeling, which is fundamental to connective tissue function. Glycosaminoglycans are selected from the group of chondroitin sulfate, heparin sulfate, and dermatan sulfate and hyaluronan. Non-glycosaminoglycan osmotic agents which may also be included are polymers such as dextran and polyvinyl pyrolodone (PVP) and amino acids such as glycine and proline.

The stabilizing solution can also contain an appropriate buffer. The nature of the buffer is important in several aspects of the processing technique. Crystalloid, low osmotic strength buffers have been associated with damage occurring during saphenous vein procurement and with corneal storage. Optimum pH and buffering capacity against the products of hypoxia damage (described below), is essential. In this context the organic and bicarbonate buffers have distinct advantages. (In red cell storage, acetate-citrate buffers with glycine and glucose have been shown to be effective in prolonging shelf-life and maintaining cellular integrity.) The inventors prefer to use an organic buffer selected from the group consisting of 2-(N-morpholino)ethanesulfonic acid (MES), 3-(N-morpholine)propanesulfonic acid (MOPS) and N-2-hydroxyethylpiperazine-N'-2-ethane-sulfonic acid (HEPES). Alternatively, a low salt or physiological buffer, including phosphate, bicarbonate and acetate-citrate, may be more appropriate in certain applications.

In another aspect, components of the stabilizing solution address one or more of the events that occur during the harvesting of tissues, such as spasm, hypoxia, hypoxia reperfusion, lysosomal enzyme release, platelet adhesion, sterility and buffering conditions. Involuntary contraction of the smooth muscles can result from mechanical stretching or distension, as well as from the chemical action of certain endothelial cell derived contraction factors, typically released under hypoxic (low oxygen) conditions. This involuntary contraction may result in damage to the adjacent ECM. For this reason, the stabilizing solution can include one or more smooth muscle relaxants, selected from the group of calcitonin gene related peptide (CGRP), papaverine, sodium nitroprusside (NaNP), H7 (a protein Kinase C inhibitor) calcium channel blockers, calcium chelators, isoproterenol, phentolamine, pinacidil, isobutylmethylxanthine (IBMX), nifedepine and flurazine. The harvested tissue can be immediately placed into this stabilizing solution and is maintained at 4° C. during transportation and any storage prior to further processing.

The tissue graft material of the invention can be provided in any suitable form, including substantially two-dimensional sheet form (optionally meshed sheet), or a three-dimensional form such as a tube, valve leaflet, or the like. The tissue graft material may contain a single layer of isolated ECM material, or may be a multilaminate construct sized the same as its component layers (e.g. containing directly overlapped layers) or larger than its component layers (e.g. containing partially overlapped layers), see, e.g., U.S. Pat. Nos. 5,885,619 and 5,711,969.

In another embodiment, the invention provides a medical product that includes a dry collagenous powder useful for example to treat wounds or to otherwise induce tissue growth at a desired implant location, and including an ECM material. The powder is desirably effective to gel upon rehydration with an aqueous medium and includes FGF-2 at a level of at least about 50 nanograms per gram dry weight. Illustratively, the powder can include a particulate of ECM material prepared by drying a fluidized material prepared as described in U.S. Pat. Nos. 5,516,533 and 5,275,826. This resulting powder can be used alone or in combination with other powder materials to support gelling of the overall powder upon rehydration with an aqueous medium such as a buffered saline solution. In this regard, in addition to the particulate ECM material, the powder composition may also include powdered, purified collagen, gelatin, or the like, to assist in gelling the product upon rehydration.

In one embodiment, the preparation of the powder will be conducted to include FGF-2 at a level of at least about 50 nanograms per gram dry weight, more preferably at least about 60, 70, 80, or 100 nanograms per gram dry weight. Resultant fluid compositions containing solubilized or suspended collagenous ECM materials will desirably be prepared to contain FGF-2 at a level of about 0.1 nanograms per milliliter or greater, e.g. typically in the range of about 0.1 nanograms per ml to about 100 nanograms per ml. This fluid composition is desirably gelable, for example upon incubation for a time after rehydration, which may be hastened by bringing the fluid composition to a relatively neutral pH and/or to body temperature from room temperature. In other embodiments, the fluidized medical product may contain FGF-2 at a level of about 1 to about 15 nanograms per ml, or may contain FGF-2 at a level of about 10 to about 30 nanograms per ml.

As disclosed above, certain embodiments of the invention provide packaged, sterile medical products. Known packaging techniques and materials can be used in the manufacture of such products, with the packaging being selected to suit the final sterilization technique being employed, e.g. ethylene oxide gas, electron-beam, or gas plasma techniques. In addition, the packaging may contain or otherwise bear indicia relating to the use of the enclosed graft material for a particular medical indication, e.g. wound care, and/or may contain or otherwise bear indicia as to one or more growth factors (e.g. FGF-2) for which the product manufacture has been controlled to modulate its level, e.g. to reflect a minimum level of such growth factor, a maximum level of such growth factor, or a range of such growth factor contained in the enclosed tissue graft product.

In other embodiments, the present invention provides ECM gel compositions and methods and materials for their preparation, which can optionally also be used in conjunction with the techniques described above for modulating the level of one or more bioactive substances in the product, including for example growth factors such as FGF-2. The gel compositions of the invention can be prepared from an isolated ECM material, for example one of those listed above. The ECM material is used to prepare a solubilized mixture including components of the material. This can be achieved by digestion of the ECM material in an acidic or basic medium and/or by contact with an appropriate enzyme or combination of enzymes.

Typically, the ECM material is reduced to particulate form to aid in the digestion step. This can be achieved by tearing, cutting, grinding or shearing the isolated ECM material. Illustratively, shearing may be conducted in a fluid medium, and grinding may be conducted with the material in a frozen state. For example, the material can be contacted with liquid nitrogen to freeze it for purposes of facilitating grinding into powder form. Such techniques can involve freezing and pulverizing submucosa under liquid nitrogen in an industrial blender.

Any suitable enzyme may be used for an enzymatic digestion step. Such enzymes include for example serine proteases, aspartyl proteases, and matrix metalloproteases. The concentration of the enzyme can be adjusted based on the specific enzyme used, the amount of submucosa to be digested, the duration of the digestion, the temperature of the reaction, and the desired properties of the final product. In one embodiment about 0.1% to about 0.2% of enzyme (pepsin, for example) is used and the digestion is conducted under cooled conditions for a period of time sufficient to substantially digest the ECM material. The digestion can be conducted at any suitable temperature, with temperatures ranging from 4-37° C. being preferred. Likewise, any suitable duration of digestion can be used, such durations typically falling in the range of about 2-180 hours. The ratio of the concentration of ECM material (hydrated) to total enzyme can be any suitable ration, for instance ranging from about 25 to about 2500; in certain aspects, this ration usually ranges from about 25 to about 125 and more typically the ratio is about 50, and the digestion is conducted at 4° C. for 24-72 hours. When an enzyme is used to aid in the digestion, the digestion will be performed at a pH at which the enzyme is active and more advantageously at a pH at which the enzyme is optimally active. Illustratively, pepsin exhibits optimal activity at pH's in the range of about 2-4.

The enzymes or other disruptive agents used to solubilize the ECM material can be removed or inactivated before or during the gelling process so as not to compromise gel formation or subsequent gel stability. Also, any disruptive agent, particularly enzymes, that remain present and active during storage of the tissue will potentially change the composition and potentially the gelling characteristics of the solution. Enzymes, such as pepsin, can be inactivated with protease inhibitors, a shift to neutral pH, a drop in temperature below 0° C., heat inactivation or through the removal of the enzyme by fractionation. A combination of these methods can be utilized to stop digestion of the ECM material at a predetermined endpoint, for example the ECM material can be immediately frozen and later fractionated to limit digestion.

The ECM material is enzymatically digested for a sufficient time to produce a hydrolysate of ECM components. The ECM can be treated with one enzyme or with a mixture of enzymes to hydrolyze the structural components of the material and prepare a hydrolysate having multiple hydrolyzed components of reduced molecular weight. The length of digestion time is varied depending on the application, and the digestion can be extended to completely solubilize the ECM material. In some modes of operation, the ECM material will be treated sufficiently to partially solubilize the material to produce a digest composition comprising hydrolyzed ECM components and nonhydrolyzed ECM components. The digest composition can then optionally be further processed to remove at least some of the nonhydrolyzed components. For example, the nonhydrolyzed components can be separated from the hydrolyzed portions by centrifugation, filtration, or other separation techniques known in the art.

Preferred gel compositions of the present invention are prepared from enzymatically digested vertebrate ECM material that has been fractionated under acidic conditions, for example including pH ranging from about 2 to less than 7, especially to remove low molecular weight components. Typically, the ECM hydrolysate is fractionated by dialysis against a solution or other aqueous medium having an acidic pH, e.g. a pH ranging from about 2 to about 5, more desirably greater than 3 and less than 7. In addition to fractionating the hydrolysate under acidic conditions, the ECM hydrolysate is typically fractionated under conditions of low ionic strength with minimal concentrations of salts such as those usually found in standard buffers such as PBS (i.e., NaCl, KCl, $Na_2HPO_4$, or $KH_2PO_4$) that can pass through the dialysis membrane and into the hydrolysate. Such fractionation conditions work to reduce the ionic strength of the ECM hydrolysate and thereby provide enhanced gel forming characteristics.

The hydrolysate solution produced by enzymatic digestion of the ECM material has a characteristic ratio of protein to carbohydrate. The ratio of protein to carbohydrate in the hydrolysate is determined by the enzyme utilized in the digestion step and by the duration of the digestion. The ratio may be similar to or may be substantially different from the protein to carbohydrate ratio of the undigested ECM tissue. For example, digestion of vertebrate ECM material with a protease such as pepsin, followed by dialysis, will form a fractionated ECM hydrolysate having a lower protein to carbohydrate ratio relative to the original ECM material.

In accordance with certain embodiments of the invention, shape retaining gel forms of ECM are prepared from ECM material that has been enzymatically digested and fractionated under acidic conditions to form an ECM hydrolysate that has a protein to carbohydrate ratio different than that of the original ECM material. Such fractionation can be achieved entirely or at least in part by dialysis. The molecular weight cut off of the ECM components to be included in the gel material is selected based on the desired properties of the gel. Typically the molecular weight cutoff of the dialysis membrane (the molecular weight above which the membrane will prevent passage of molecules) is within in the range of about 2000 to about 10000 Dalton, and more preferably from about 3500 to about 5000 Dalton. In once such embodiment, the digested/solubilized extracellular matrix composition is dialyzed against an acidic solution having a low ionic strength. For example, the solubilized extracellular matrix composition can be dialyzed against a hydrochloric acid solution, but any other acids including acetic acid, formic acid, lactic acid, citric acid, sulfuric acid, ethanoic acid, carbonic acid, nitric acid, or phosphoric acid can be used. In various illustrative embodiments, the fractionation, for example by dialysis, can be performed at about 2° C. to about 37° C. for about 1 hour to about 96 hours. In another illustrative embodiment, and the concentration of the acid, such as acetic acid, hydrochloric acid, formic acid, lactic acid, citric acid, sulfuric acid, ethanoic acid, carbonic acid nitric acid, or phosphoric acid, against which the solubilized extracellular matrix composition is dialyzed can be from about 0.001 N to about 0.1 N, from about 0.005 N to about 0.1 N, from about 0.01 N to about 0.1 N, from about 0.05 N to about 0.1 N, from about 0.001 N to about 0.05 N, about 0.001 N to about 0.01 N, or from about 0.01 N to about 0.05 N. In one illustrative embodiment, the solubilized extracellular matrix composition can be dialyzed against 0.01 N HCl. However, the fractionation can be performed at any temperature, for any length of time, and against any concentration of acid. In one embodiment of the invention, apart from the potential removal of undigested ECM components after the digestion step and any controlled fractionation to remove low molecular weight components as discussed above, the ECM hydrolysate is processed so as to avoid any substantial further physical separation of the ECM components. For example, when a more concentrated ECM hydrolysate material is desired, this can be accomplished by removing water from the system (e.g. by evaporation or lyophilization) as opposed to using conventional "salting out"/ centrifugation techniques that would demonstrate significant selectivity in precipitating and isolating collagen, leaving behind amounts of other desired ECM components. Thus, in certain embodiments of the invention, solubilized ECM components of the ECM hydrolysate remain substantially unfractionated, or remain substantially unfractionated above a predetermined molecular weight cutoff such as that used in the dialysis membrane, e.g. above a given value in the range of about 2000 to 10000 Dalton, more preferably about 3500 to about 5000 Dalton.

In another embodiment, the source extracellular matrix material can be extracted in addition to being solubilized with an acid and/or treated with an enzyme. Extraction methods for extracellular matrices are known to those skilled in the art and are described in detail in U.S. Pat. No. 6,375,989, incorporated herein by reference. Illustrative extraction excipients include, for example, chaotropic agents such as urea, guanidine, sodium chloride or other neutral salt solutions, magnesium chloride, and non-ionic or ionic surfactants.

Vertebrate ECM material can be stored frozen (e.g. at about −20 to about −80° C.) in either its solid, comminuted or enzymatically digested forms prior to formation of the gel compositions of the present invention, or the material can be stored after being hydrolyzed and fractionated. The ECM material can be stored in solvents that maintain the collagen in its native form and solubility. For example, one suitable storage solvent is 0.01 M acetic acid, however other acids can be substituted, such as 0.01 N HCl. In accordance with one embodiment the fractionated ECM hydrolysate is dried (by lyophilization, for example) and stored in a dehydrated/lyophilized state. The dried form can be rehydrated and gelled to form a gel of the present invention.

In this regard, an ECM hydrolysate as described herein (fractionated or unfractionated) can be dried to form a powder or other dried solid composition in any suitable manner. In certain embodiments a liquid medium containing the ECM hydrolysate is dried under lyophilization conditions or other similar conditions that involve the removal of water and/or another hydrant by sublimation from solid to gas. In one aspect, a solubilized extracellular matrix composition is lyophilized after an enzymatic digestion as described herein. In another aspect, a solubilized extracellular matrix composition is lyophilized after an enzymatic digestion and subsequent separation step that removes any insoluble components. In yet another aspect, the solubilized extracellular matrix composition is lyophilized after digestion and fractionation steps as described herein. In another embodiment, a polymerized matrix formed with a solubilized extracellular matrix composition as described herein is lyophilized. In one illustrative mode of carrying out lyophilization steps as described herein, the solubilized extracellular matrix composition is first frozen, and then placed under a vacuum. In another lyophilization embodiment, the solubilized extracellular matrix composition is freeze-dried under a vacuum. Any method of lyophilization known to the skilled artisan can be used.

If the solubilized extracellular matrix composition is lyophilized, the lyophilized extracellular matrix composition can be stored frozen or at room temperature (for example, at about −80° C. to about 25° C.). Storage temperatures are selected to stabilize the solubilized extracellular matrix components. The compositions can be stored for about 1-26 weeks, or longer. In one illustrative embodiment, a lyophilized or otherwise dried extracellular matrix composition will include an acid as a storage excipient, for example deriving from an acid present in an aqueous or other liquid medium containing the solubilized extracellular matrix composition that is subjected to lyophilization or other drying conditions. In certain embodiments, hydrochloric acid is included in the lyophilized or otherwise dried extracellular matrix composition. As examples, hydrochloric acid, or other acids, at concentrations of from about 0.001 N to about 0.1 N, from about 0.005 N to about 0.1 N, from about 0.01 N to about 0.1 N, from about 0.05 N to about 0.1 N, from about 0.001 N to about 0.05 N, from about 0.001 N to about 0.01 N, or from about 0.01 N to about 0.05 N can be used as a storage excipient for the lyophilized/dried, solubilized extracellular matrix components. Other acids can be used as storage excipients including for instance acetic acid, formic acid, lactic acid, citric acid, sulfuric acid, ethanoic acid, carbonic acid, nitric acid, or phosphoric acid, and these acids can be used at any of the above-described concentrations. In one illustrative embodiment, a lyophilizate or other dried material can be prepared from an acidic medium, such as an acetic acid medium, at a concentration of from about 0.001 M to about 0.5 M or from about 0.01 M to about 0.5 M. In another embodiment, a lyophilizate or other dried material can be prepared from an aqueous medium with a pH of about 6 or below. In other illustrative embodiments, lyoprotectants, cryoprotectants, lyophilization accelerators, or crystallizing excipients (e.g., ethanol, isopropanol, mannitol, trehalose, maltose, sucrose, tert-butanol, and tween 20), or combinations thereof, and the like can be present during lyophilization.

In accordance with one embodiment, the fractionated ECM hydrolysate will exhibit the capacity to gel upon adjusting the pH of a relatively more acidic aqueous medium containing it to about 5 to about 9, more preferably about 6.6 to about 8.0, and typically about 7.2 to about 7.8, thus inducing fibrillogenesis and matrix gel assembly. In one embodiment, the pH of the fractionated hydrolysate is adjusted by the addition of a buffer that does not leave a toxic residue, and has a physiological ion concentration and the capacity to hold physiological pH. Examples of suitable buffers include PBS, HEPES, and DMEM. In one embodiment the pH of the fractionated ECM hydrolysate is raised by the addition of a buffered NaOH solution to 6.6 to 8.0, more preferably 7.2 to 7.8. Any suitable concentration of NaOH solution can be used for these purposes, for example including about 0.05 M to about 0.5 M NaOH. In accordance with one embodiment, the ECM hydrolysate is mixed with a buffer and sufficient 0.25 N NaOH is added to the mixture to achieve the desired pH. If desired at this point, the resultant mixture can be aliquoted into appropriate forms or into designated cultureware and incubated at 37° C. for 0.5 to 1.5 hours to form an ECM gel.

The ionic strength of the ECM hydrolysate is believed to be important in maintaining the fibers of collagen in a state that allows for fibrillogenesis and matrix gel assembly upon neutralization of the hydrolysate. Accordingly, if needed, the salt concentration of the ECM hydrolysate material can be reduced prior to neutralization of the hydrolysate. The neutralized hydrolysate can be caused to gel at any suitable temperature, e.g. ranging from about 4° C. to about 40° C. The temperature will typically affect the gelling times, which may range from 5 to 120 minutes at the higher gellation temperatures and 1 to 8 hours at the lower gellation temperatures. Typically, the hydrolysate will be gelled at elevated temperatures to hasten the gelling process, for example at 37° C. In this regard, preferred neutralized ECM hydrolysates will be effective to gel in less than about ninety minutes at 37° C., for example approximately thirty to ninety minutes at 37° C. Alternatively, the gel can be stored at 4° C., and under these conditions the setting of the gel will be delayed, e.g. for about 3-8 hours.

Additional components can be added to the hydrolysate composition before, during or after forming the gel. For example, proteins carbohydrates, growth factors, therapeutics, bioactive agents, nucleic acids, cells or pharmaceuticals can be added. In certain embodiments, such materials are added prior to formation of the gel. This may be accomplished for example by forming a dry mixture of a powdered ECM hydrolysate with the additional component(s), and then reconstituting and gelling the mixture, or by incorporating the additional component(s) into an aqueous, ungelled composition of the ECM hydrolysate before, during (e.g. with) or after addition of the neutralization agent. In other embodiments, the additional component(s) are added to the formed ECM gel, e.g. by infusing or mixing the component(s) into the gel and/or coating them onto the gel.

In one embodiment of the invention, a particulate ECM material will be added to the hydrolysate composition, which will then be incorporated in the formed gel. Such particulate ECM materials can be prepared by cutting, tearing, grinding or otherwise comminuting an ECM starting material. For example, a particulate ECM material having an average particle size of about 50 microns to about 500 microns may be included in the hydrolysate, more preferably about 100 microns to about 400 microns. The ECM particulate can be added in any suitable amount relative to the hydrolysate, with preferred ECM particulate to ECM hydrolysate weight ratios (based on dry solids) being about 0.1:1 to about 200:1, more preferably in the range of 1:1 to about 100:1. The inclusion of such ECM particulates in the ultimate gel can serve to provide additional material that can function to provide bioactivity to the gel (e.g. itself including FGF-2 and/or other growth factors or bioactive substances as discussed herein) and/or serve as scaffolding material for tissue ingrowth.

In certain embodiments, a solubilized extracellular matrix composition as described herein can be sterilized in any suitable manner. Exemplary sterilizing agents and techniques are described above, but any sterilizing agent or method of sterilization known in the art can be used. For example, a solubilized extracellular matrix composition can be sterilized using glutaraldehyde, formaldehyde, acidic pH, propylene oxide, ethylene oxide, gas plasma sterilization, gamma radiation, electron beam sterilization, or peracetic acid sterilization, or combinations thereof, and the like. Sterilization techniques which do not adversely affect the structure and biotropic properties of the components of the solubilized extracellular matrix composition can be used.

In certain embodiments, an ECM hydrolysate material to be used in tissue augmentation, e.g. in functional or cosmetic purposes, will incorporate an ECM particulate material. In these embodiments, the ECM particulate material can be included at a size and in an amount that effectively retains an injectable character to the hydrolysate composition, for example by injection through a needle having a size in the range of 18 to 31 gauge (internal diameters of 0.047 inches to about 0.004 inches). In this fashion, non-invasive procedures for tissue augmentation will be provided, which in preferred cases will involve the injection of an ungelled ECM hydrolysate containing suspended ECM particles at a relatively lower (e.g. room) temperature, which will be promoted to form a gelled composition when injected into a patient and thereby brought to physiologic temperature (about 37° C.).

In other aspects of the invention, it has been discovered that processing techniques that involve contacting the ECM material with a disinfecting oxidizing agent compound can significantly affect not only the concentration of bioactive substances but also the gelling quality of the collagen molecules. In particular, it has been found that contacting an ECM material with an oxidizing agent such as peracetic acid prior to digestion to form the ECM hydrolysate can disrupt or impair the ability of ECM hydrolysate to form a gel. On the other hand, contacting an aqueous medium including ECM hydrolysate components with an oxidizing disinfectant such as a peroxy compound provides an improved ability to recover a disinfected ECM hydrolysate that exhibits the capacity to form beneficial gels. In accordance with one embodiment of the invention, an aqueous medium containing ECM hydrolysate components is disinfected by providing a peroxy disinfectant in the aqueous medium. This is advantageously achieved using dialysis to deliver the peroxy disinfectant into and/or to remove the peroxy disinfectant from the aqueous medium containing the hydrolysate. In one preferred embodiment, the aqueous medium containing the ECM hydrolysate is dialyzed against an aqueous medium containing the peroxy disinfectant to deliver the disinfectant into contact with the ECM hydrolysate, and then is dialyzed against an appropriate aqueous medium (e.g. an acidic aqueous medium) to at least substantially remove the peroxy disinfectant from the ECM hydrolysate. During this dialysis step, the peroxy compound passes through the dialysis membrane and into the ECM hydrolysate, and contacts ECM components for a sufficient period of time to disinfect the ECM components of the hydrolysate. In this regard, typical contact times will range from about 0.5 hours to about 8 hours and more typically about 1 hour to about 4 hours. The period of contact will be sufficient to substantially disinfect the digest, including the removal of endotoxins and inactivation of virus material present. The removal of the peroxy disinfectant by dialysis may likewise be conducted over any suitable period of time, for example having a duration of about 4 to about 180 hours, more typically about 24 to about 96 hours. In one embodiment, the sterilized, solubilized extracellular matrix composition can be dialyzed against 0.01 N HCl, for example, prior to lyophilization to remove the sterilization solution and so that the solubilized extracellular matrix components are in a 0.01 N HCl solution when lyophilized. Alternatively, the solubilized extracellular matrix composition can be dialyzed against acetic acid, for example, prior to lyophilization and can be lyophilized in acetic acid and redissolved in HCl or water. In general, the disinfection step will desirably result in a disinfected ECM hydrolysate composition having sufficiently low levels of endotoxins, viral burdens, and other contaminant materials to render it suitable for medical use. Endotoxin levels below about 2 endotoxin units (EUs) per gram (dry weight) are preferred, more preferably below about 1 EU per gram, as are virus levels below 100 plaque forming units per gram (dry weight), more preferably below 1 plaque forming unit per gram.

In one embodiment, the aqueous ECM hydrolysate composition is a substantially homogeneous solution during the dialysis step for delivering the oxidizing disinfectant to the hydrolysate composition and/or during the dialysis step for removing the oxidizing disinfectant from the hydrolysate composition. Alternatively, the aqueous hydrolysate composition can include suspended ECM hydrolysate particles, optionally in combination with some dissolved ECM hydrolysate components, during either or both of the oxidizing disinfectant delivery and removal steps. Dialysis processes in which at least some of the ECM hydrolysate components are dissolved during the disinfectant delivery and/or removal steps are preferred and those in which substantially all of the ECM hydrolysate components are dissolved are more preferred.

The disinfection step can be conducted at any suitable temperature, and will typically be conducted between 0° C. and 37° C., more typically between about 4° C. and about 15° C. During this step, the concentration of the ECM hydrolysate solids in the aqueous medium is typically in the range of about 2 mg/ml to about 200 mg/ml, and may vary somewhat through the course of the dialysis due to the migration of water through the membrane. In certain embodiments of the invention, a relatively unconcentrated digest is used, having a starting ECM solids level of about 5 mg/ml to about 15 mg/ml. In other embodiments of the invention, a relatively concentrated ECM hydrolysate is used at the start of the disinfection step, for example having a concentration of at least about 20 mg/ml and up to about 200 mg/ml, more preferably at least about 100 mg/ml and up to about 200 mg/ml. It has been found that the use of concentrated ECM hydrolysates during this disinfection processing results in an ultimate gel composition having higher gel strength than that obtained using similar processing with a lower concentration ECM hydrolysate. Accordingly, processes which involve the removal of amounts of water from the ECM hydrolysate resulting from the digestion prior to the disinfection processing step are preferred. For example, such processes may include removing only a portion of the water (e.g. about 10% to about 98% by weight of the water present) prior to the dialysis/disinfection step, or may include rendering the digest to a solid by drying the material by lyophilization or otherwise, reconstituting the dried material in an aqueous medium, and then treating that aqueous medium with the dialysis/disinfection step.

Certain impacts of dialysis processing conditions upon ECM hydrolysate gels are illustrated in specific work to date described more particularly in Examples 2-5 below. Generally, several different submucosa hydrolysates were prepared while varying the acid present during pepsin digestion and varying the concentration of ECM hydrolysate present during dialysis against a peracetic acid (PAA) solution. Specifically, a first gel (A1) was prepared using 0.5 M acetic acid in the pepsin digestion solution, and about 5-15 mg/ml ECM hydrolysate during the PAA disinfection; a second gel (A2) was prepared using 0.5 M acetic acid in the pepsin digestion solution, and about 130-150 mg/ml ECM hydrolysate during the PAA disinfection; a third gel (H1) was prepared using 0.01 M hydrochloric acid in the pepsin digestion solution, and about 5-15 mg/ml ECM hydrolysate during the PAA disinfection; and a fourth gel (H2) was prepared using 0.01 M hydrochloric acid in the pepsin digestion solution, and about 130-150 mg/ml ECM hydrolysate during the PAA disinfection. The processed ECM hydrolysates were provided in a solution of 0.1 M HCl at a concentration of about 30 mg/ml, and then PBS was added and the pH of the mixture was adjusted to 7.5-7.6 with 0.25 M NaOH to gel the composition. The mechanical properties of the various gels were then assessed. The results are summarized in Table 1 below.

TABLE 1

| Gel | Compressive Modulus (kPa) | Compressive Strength (kPa |
|-----|---------------------------|---------------------------|
| A1  | 1                         | 0.5                       |
| A2  | 7                         | 2                         |
| H1  | 10                        | 3                         |
| H2  | 20                        | 7                         |

As can be seen, the gels prepared using high submucosa hydrolysate concentrations during the disinfection step (A2, H2) were relatively stronger than those prepared using low submucosa hydrolysate concentrations (A1, H1). In addition, in cell growth assays, the A2 and H2 gels demonstrated an improved capacity to support the proliferation of primary human dermal fibroblast and primary human bladder smooth muscle cells as compared to the A1 and H1 gels. In other observations, the gels prepared from ECM hydrolysate materials resultant of HCl/pepsin digestion were relatively stronger than the corresponding gels resultant of acetic acid/pepsin digestion. Thus, the conditions used during the preparation and processing of ECM hydrolysate materials can be selected and controlled to modulate the physical and biological properties of the ultimate ECM gel compositions.

In one mode of operation, the disinfection of the aqueous medium containing the ECM hydrolysate can include adding the peroxy compound or other oxidizing disinfectant directly to the ECM hydrolysate, for example being included in an aqueous medium used to reconstitute a dried ECM hydrolysate or being added directly to an aqueous ECM hydrolysate composition. The disinfectant can then be allowed to contact the ECM hydrolysate for a sufficient period of time under suitable conditions (e.g. as described above) to disinfect the hydrolysate, and then removed from contact with the hydrolysate. In one embodiment, the oxidizing disinfectant can then be removed using a dialysis procedure as discussed above. In other embodiments, the disinfectant can be partially or completely removed using other techniques such as chromatographic or ion exchange techniques, or can be partially or completely decomposed to physiologically acceptable components. For example, when using an oxidizing disinfectant containing hydrogen peroxide (e.g. hydrogen peroxide alone or a peracid such as peracetic acid), hydrogen peroxide can be allowed or caused to decompose to water and oxygen, for example in some embodiments including the use of agents that promote the decomposition such as thermal energy or ionizing radiation, e.g. ultraviolet radiation.

In another mode of operation, the oxidizing disinfectant can be delivered into the aqueous medium containing the ECM hydrolysate by dialysis and processed sufficiently to disinfect the hydrolysate (e.g. as described above), and then removed using other techniques such as chromatographic or ion exchange techniques in whole or in part, or allowed or caused to decompose in whole or in part as discussed immediately above.

Peroxygen compounds that may be used in the disinfection step include, for example, hydrogen peroxide, organic peroxy compounds, and preferably peracids. Such disinfecting agents are used in a liquid medium, preferably a solution, having a pH of about 1.5 to about 10.0, more desirably about 2.0 to about 6.0. As to peracid compounds that can be used, these include peracetic acid, perpropioic acid, or perbenzoic acid. Peracetic acid is the most preferred disinfecting agent for purposes of the present invention.

When used, peracetic acid is desirably diluted into about a 2% to about 50% by volume of alcohol solution, preferably ethanol. The concentration of the peracetic acid may range, for instance, from about 0.05% by volume to about 1.0% by volume. Most preferably, the concentration of the peracetic acid is from about 0.1% to about 0.3% by volume. When hydrogen peroxide is used, the concentration can range from about 0.05% to about 30% by volume. More desirably the hydrogen peroxide concentration is from about 1% to about 10% by volume, and most preferably from about 2% to about 5% by volume. The solution may or may not be buffered to a pH from about 5 to about 9, with more preferred pH's being from about 6 to about 7.5. These concentrations of hydrogen peroxide can be diluted in water or in an aqueous solution of about 2% to about 50% by volume of alcohol, most preferably ethanol. Additional information concerning preferred peroxy disinfecting agents can be found in discussions in U.S. Pat. No. 6,206,931, which is herein incorporated by reference.

In one illustrative embodiment, a digested/solubilized extracellular matrix composition is directly sterilized, for instance before any solids separation step, for example, with peracetic acid or with peracetic acid and ethanol (e.g., by the addition of 0.18% peracetic acid and 4.8% ethanol to the solubilized extracellular matrix composition before the separation step). In another embodiment, sterilization can be carried out during a fractionation step. For example, a solubilized extracellular matrix composition can be dialyzed against chloroform, peracetic acid, or a solution of peracetic acid and ethanol to disinfect or sterilize the solubilized extracellular matrix composition. Illustratively, the solubilized extracellular matrix composition can be sterilized by dialysis against a solution of peracetic acid and ethanol (e.g., 0.18% peracetic acid and 4.8% ethanol). The chloroform, peracetic acid, or peracetic acid/ethanol can be removed prior to lyophilization, for example by dialysis against an acid, such as 0.01 N HCl. In an alternative embodiment, the lyophilized composition can be sterilized directly after rehydration, for example, by the addition of 0.18% peracetic acid and 4.8% ethanol. In this embodiment, the sterilizing agent can be removed prior to polymerization of the solubilized extracellular matrix components to form fibrils.

ECM gel materials of the present invention can be prepared to have desirable properties for handling and use. For example, fluidized ECM hydrolysates can be prepared in an aqueous medium, which can thereafter be caused or allowed to form of a gel. Such prepared aqueous mediums can have any suitable level of ECM hydrolysate therein for subsequent gel formation. Typically, the ECM hydrolysate will be present in the aqueous medium to be gelled at a concentration of about 2 mg/ml to about 200 mg/ml, more typically about 20 mg/ml to about 200 mg/ml, and in some preferred embodiments about 30 mg/ml to about 120 mg/ml. In preferred forms, the aqueous ECM hydrolysate composition to be gelled will have an injectable character, for example by injection through a needle having a size in the range of 18 to 31 gauge (internal diameters of about 0.047 inches to about 0.004 inches).

If the solubilized extracellular matrix composition is lyophilized or otherwise dried, the resulting dried material can be redissolved in any suitable liquid medium. In certain embodiments, the dried material can be redissolved in an acidic solution or in water. The lyophilizate or other dried material can be redissolved in, for example, acetic acid, hydrochloric acid, formic acid, lactic acid, citric acid, sulfuric acid, ethanoic acid, carbonic acid, nitric acid, or phosphoric acid, at any of the above-described concentrations, or can be redissolved in water. In one illustrative embodiment, the lyophilizate or other dried material is redissolved in 0.01 N HCl. For use in producing engineered ECM-based matrices that can be injected in vivo or used for other purposes in vitro, the redissolved lyophilizate can be subjected to varying conditions (e.g., pH, phosphate concentration, temperature, buffer composition, ionic strength, and composition and concentration of solubilized extracellular matrix composition components (dry weight/ml)) that result in polymerization to form engineered ECM-based matrices for specific tissue graft applications.

Furthermore, gel compositions can be prepared so that in addition to neutralization, heating to physiologic temperatures (such as 37° C.) will substantially reduce the gelling time of the material. As well, once the material is gelled, it can optionally be dried to form a sponge solid material. It is contemplated that commercial products may constitute any of the these forms of the ECM gel composition, e.g. (i) packaged, sterile powders which can be reconstituted in an acidic medium and neutralized and potentially heated to form a gel, (ii) packaged, sterile aqueous compositions including solubilized ECM hydrolysate components under non-gelling (e.g. acidic) conditions; (iii) packaged, sterile gel compositions, and (iv) packaged, sterile, dried sponge compositions; or other suitable forms. In one embodiment of the invention, a medical kit is provided that includes a packaged, sterile aqueous composition including solubilized ECM hydrolysate components under non-gelling (e.g. acidic) conditions, and a separately packaged, sterile aqueous neutralizing composition (e.g. containing a buffer and/or base) that is adapted to neutralize the ECM hydrolysate medium for the formation of a gel. In another embodiment of the invention, a medical kit includes a packaged, sterile, dried (e.g. lyophilized) ECM hydrolysate powder, a separately packaged, sterile aqueous acidic reconstituting medium, and a separately packaged sterile, aqueous neutralizing medium. In use, the ECM hydrolysate powder can be reconstituted with the reconstituting medium to form a non-gelled mixture, which can then be neutralized with the neutralizing medium for the formation of the gel.

Medical kits as described above may also include a device, such as a syringe, for delivering the neutralized ECM hydrolysate medium to a patient. In this regard, the sterile, aqueous ECM hydrolysate medium or the sterile ECM hydrolysate powder of such kits can be provided packaged in a syringe or other delivery instrument. In addition, the sterile reconstituting and/or neutralizing medium can be packaged in a syringe, and means provided for delivering the contents of the syringe into to another syringe containing the aqueous ECM hydrolysate medium or the ECM hydrolysate powder for mixing purposes. In still other forms of the invention, a self-gelling aqueous ECM hydrolysate composition can be packaged in a container (e.g. a syringe) and stable against gel formation during storage. For example, gel formation of such products can be dependent upon physical conditions such as temperature or contact with local milieu present at an implantation site in a patient. Illustratively, an aqueous ECM hydrolysate composition that does not gel or gels only very slowly at temperatures below physiologic temperature (about 37° C.) can be packaged in a syringe or other container and potentially cooled (including for example frozen) prior to use for injection or other implantation into a patient.

In particular applications, ECM hydrolysate compositions that form hydrogels at or near physiologic pH and temperature will be preferred for in vivo bulking applications, for example in the treatment of stress urinary incontinence, gastroesophageal reflux disease, cosmetic surgery, vesico urethral reflux, anal incontinence and vocal cord repair. These forms of the submucosa or other ECM gel have, in addition to collagen, complex extracellular matrix sugars and varying amounts of growth factors in other bioactive agents that can serve to remodel tissue at the site of implantation. These ECM hydrolysate compositions can, for example, be injected into a patient for these applications.

ECM gels and dry sponge form materials of the invention prepared by drying ECM gels can be used, for example, in wound healing and/or tissue reconstructive applications, or in the culture of cells.

Generally, it has been found that the manipulations used to prepare ECM hydrolysate compositions and gellable or gelled forms thereof can also have a significant impact upon growth factors or other ECM components that may contribute to bioactivity. Techniques for modulating and sampling for levels of FGF-2 or other growth factors or bioactive substances can also be used in conjunction with the manufacture of the described ECM hydrolysate compositions of the invention. Illustratively, it has been discovered that the dialysis/disinfection processes of the invention employing peroxy compounds typically cause a reduction in the level of FGF-2 in the ECM hydrolysate material. In work to date as described in Examples 2-5, such processing using peracetic acid as disinfectant has caused a reduction in the level of FGF-2 in the range of about 30% to about 50%. Accordingly, to retain higher levels of FGF-2, one can process for a minimal about of time necessary to achieve the desired disinfection of the material; on the other hand, to reduce the FGF-2 to lower levels, the disinfection processing can be continued for a longer period of time. In one embodiment of the invention, the disinfection process and subsequent steps will be sufficiently conducted to result in a medically sterile aqueous ECM hydrolysate composition, which can be packaged using sterile filling operations. In other embodiments, any terminal sterilization applied to the ECM hydrolysate material (e.g. in dried powder, non-gelled aqueous medium, gelled or sponge form) can also be selected and controlled to optimize the level of FGF-2 or other bioactive substances in the product. Terminal sterilization methods may include, for example, high or low temperature ethylene oxide, radiation such as E-beam, gas plasma (e.g. Sterrad), or hydrogen peroxide vapor processing.

Preferred, packaged, sterilized ECM hydrolysate products prepared in accordance with the invention will have an FGF-2 level (this FGF-2 being provided by the ECM hydrolysate) of about 100 ng/g to about 5000 ng/g based upon the dry weight of the ECM hydrolysate. More preferably, this value will be about 300 ng/g to about 4000 ng/g. As will be understood, such FGF-2 levels can be determined using standard ELISA tests (e.g. using the Quantikine Human Basic Fibroblast Growth Factor ELISA kit commercially available from R&D Systems).

In order to promote a further understanding of the present invention and its features and advantages, the following specific examples are provided. It will be understood that these examples are illustrative and are not limiting of the invention.

Example 1

Small intestinal submucosa material was harvested and disinfected with peracetic acid as described in U.S. Pat. No. 6,206,931. The submucosa material was lyophilized, packaged in medical packaging comprised of polyester/Tyvek and sterilized by various methods including ethylene oxide (EO), gas plasma (hydrogen peroxide vapor), and E-beam radiation (20 kGy (plus/minus 2 kGy). The resultant submucosa material was frozen in liquid nitrogen and ground to a powder. The material was then extracted with an extraction buffer containing 2M urea, 2.5 mg/ml heparin, and 50 mM Tris buffer, at pH 7.5 at 4° C. under constant stirring for 24 hours. After 24 hours, the extraction medium was transferred to centrifuge tubes and the insoluble fraction pelleted at 12000×G. The supernatant was transferred to dialysis tubing (MW cutoff 3500) and dialyzed exhaustively against high purity (18 megaohm) water. Following dialysis the dialysate was centrifuged at 12000×G to remove any additional particulate matter and the resulting soluble extract was lyophilized. Prior to measurement the extract was reconstituted at 10 mg/dry weight per ml in the manufacturer-provided diluent (R&D Systems). Samples were centrifuged to remove any insoluble matter. The resulting supernatents were recovered and assayed for FGF-2 content using the Quantikine Human Basic Fibroblast Growth Factor Immunoassay (R&D Systems). The results are summarized in Table 2 below.

TABLE 2

ELISA Summary - CBI Extracted Tissues

| Sterilization | Growth factor range (ng/g) | % of Non-sterile* |
|---|---|---|
| NONE | 100-210 | 100 |
| EO (low temp) | 28-50 | 24 |
| EO (high temp) | 18-40 | 18 |
| E-beam | 50-150 | 66 |
| Gas Plasma | 30-125 | 49 |

*based upon the average of 8 experiments.

As can be seen, E-beam and gas plasma sterilization had a significantly lower impact in reducing the level of extractable, bioactive FGF-2 in the materials. On the other hand, ethylene oxide sterilization at both low and high temperatures had a significant impact in lowering the level of extractable, bioactive FGF-2.

Example 2

Raw (isolated/washed but non-disinfected) porcine small intestine submucosa was frozen, cut into pieces, and cryo-ground to powder with liquid nitrogen. 50 g of the submucosa powder was mixed with one liter of a digestion solution containing 1 g of pepsin and 0.5 M acetic acid. The digestion process was allowed to continue for 48-72 hours under constant stirring at 4° C. At the end of the process, the digest was centrifuged to remove undigested material. The acetic acid was then removed by dialysis against 0.01 M HCl for approximately 96 hours at 4° C. The resulting digest was transferred (without concentration) into a semipermeable membrane with a molecular weight cut off of 3500, and dialyzed for two hours against a 0.2 percent by volume peracetic acid in a 5 percent by volume aqueous ethanol solution at 4° C. This step served both to disinfect the submucosa digest and to fractionate the digest to remove components with molecular weights below 3500. The PAA-treated digest was then dialysed against 0.01 M HCl for 48 hours at 4° C. to remove the peracetic acid. The sterilized digest was concentrated by lyophilization, forming a material that was reconstituted at about 30 mg/ml solids in 0.01 M HCl and neutralized with phosphate buffered NaOH to a pH of about 7.5-7.6 and heated to physiologic temperature to form a submucosa gel.

Example 3

A second acetic acid processed submucosa gel was made using a process similar to that described in Example 2 above, except concentrating the digest prior to the PAA treatment. Specifically, immediately following the removal of acetic acid by dialysis, the digest was lyophilized to dryness. A concentrated paste of the digest was made by dissolving a pre-weighed amount of the lyophilized product in a known amount of 0.01 M HCl to prepare a mixture having an ECM solids concentration of about 50 mg/ml. The concentrated paste was then dialysed against the PAA solution for 2 hours and then against 0.01 M HCl for removal of PAA in the same manner described in Example 2. The digest was adjusted to about 30 mg/ml solids and neutralized with phosphate buffered NaOH to a pH of about 7.5-7.6 and heated to physiologic temperature to form a submucosa gel.

Example 4

An HCl processed submucosa gel was made using a procedure similar to that described in Example 2, except using 0.01 M of HCl in the pepsin/digestion solution rather than the 0.5 M of acetic acid, and omitting the step involving removal of acetic acid since none was present. The digest was used to form a gel as described in Example 2.

Example 5

Another HCl processed submucosa gel was made using a procedure similar to that described in Example 3, except using 0.01 M of HCl in the pepsin/digestion solution rather than the 0.5 M of acetic acid, and omitting the step involving removal of acetic acid since none was present. The digest was used to form a gel as described in Example 3.

Example 6

Preparation of Lyophilized, Bioactive ECM Composition

Small intestinal submucosa is harvested and prepared from freshly euthanized pigs (Delphi Ind.) as previously disclosed in U.S. Pat. No. 4,956,178. Intestinal submucosa is powderized under liquid nitrogen and stored at −80oC prior to use.

Digestion and solubilization of the material is performed by adding 5 grams of powdered tissue to each 100 ml of solution containing 0.1% pepsin in 0.01 N hydrochloric acid and incubating for 72 hours at 4° C. Following the incubation period, the resulting solubilized composition is centrifuged at 12,000 rpm for 20 minutes at 4° C. and the insoluble pellet is discarded. The supernatant is dialyzed against at least ten changes of 0.01 N hydrochloric acid at 4° C. (MWCO 3500) over a period of at least four days. The solubilized fractionated composition is then sterilized by dialyzing against 0.18% peracetic acid/4.8% ethyl alcohol for about two hours. Dialysis of the composition is continued for at least two more days, with three additional changes of sterile 0.01 N hydrochloric acid per day, to eliminate the peracetic acid. The contents of the dialysis bags are then lyophilized to dryness and stored.

Example 7

Preparation of Lyophilized, Bioactive ECM Composition

Small intestinal submucosa was harvested and prepared from freshly euthanized pigs (Delphi Ind.) as previously disclosed in U.S. Pat. No. 4,956,178. Intestinal submucosa was powderized under liquid nitrogen and stored at −80° C. prior to use. Digestion and solubilization of the material was performed by adding 5 grams of powdered tissue to each 100 ml of solution containing 0.1% pepsin in 0.01 N hydrochloric acid and incubating for 72 hours at 4° C. Following the incubation period, the solubilized composition was centrifuged at 12,000 rpm for 20 minutes at 4° C. and the insoluble pellet was discarded. The supernatant was lyophilized to dryness and stored.

Example 8

Preparation of Reconstituted, Bioactive ECM Composition

Immediately prior to use, lyophilized material from Example 2, consisting of a mixture of extracellular matrix components, was reconstituted in 0.01 N HCl. To polymerize the soluble extracellular matrix components into a 3-dimensional matrix, reconstituted extracellular matrix solutions were diluted and brought to a particular pH, ionic strength, and phosphate concentration by the addition of a phosphate buffer and concentrated HCl and NaOH solutions. Polymerization of neutralized solutions was then induced by raising the temperature from 4° C. to 37° C. Various initiation buffers were used to make final solutions with the properties shown in Table 3. Ionic strength was varied based on sodium chloride concentration. The pH of the polymerization reaction was controlled by varying the ratios of mono- and diabasic phosphate salts.

TABLE 3

| pH | I | [Pi] | [C] |
|---|---|---|---|
| Series 1 SIS formulations | | | |
| 6.5 | 0.16 | 0.01 | 1 mg/ml |
| 7.0 | 0.16 | 0.01 | 1 mg/ml |
| 7.4 | 0.17 | 0.01 | 1 mg/ml |
| 8.0 | 0.17 | 0.01 | 1 mg/ml |
| 8.5 | 0.17 | 0.01 | 1 mg/ml |
| 9.0 | 0.17 | 0.01 | 1 mg/ml |
| Series 2 SIS formulations | | | |
| 7.4 | 0.06 | 0.02 | 1 mg/ml |
| 7.4 | 0.30 | 0.02 | 1 mg/ml |
| 7.4 | 0.60 | 0.02 | 1 mg/ml |
| 7.4 | 0.90 | 0.02 | 1 mg/ml |
| 7.4 | 1.20 | 0.02 | 1 mg/ml |
| 7.4 | 1.20 | 0.02 | 1 mg/ml |
| Series 3 SIS formulations | | | |
| 7.4 | 0.3 | 0.00 | 1 mg/ml |
| 7.4 | 0.3 | 0.02 | 1 mg/ml |
| 7.4 | 0.3 | 0.04 | 1 mg/ml |
| 7.4 | 0.3 | 0.06 | 1 mg/ml |
| 7.4 | 0.3 | 0.08 | 1 mg/ml |
| 7.4 | 0.3 | 0.11 | 1 mg/ml |

Table 3: Engineered ECMs representing a complex mixture of interstitial ECM components (SIS) were prepared at varied pH (series 1), ionic strength (series 2), and phosphate concentration (series 3). [C] represents collagen concentration in mg/ml, [Pi] represents phosphate concentration in M, and I represents ionic strength in M.

Example 9

Preparation of Reconstituted Bioactive Extracellular Matrices

Small intestinal submucosa was harvested and prepared from freshly euthanized pigs (Delphi Ind.) as previously disclosed in U.S. Pat. No. 4,956,178. Intestinal submucosa was powderized under liquid nitrogen and stored at −80° C. prior to use. Digestion and solubilization of the material was performed by adding 5 grams of powdered tissue to each 100 ml of solution containing 0.1% pepsin in 0.01 N hydrochloric acid and incubating with stirring for 72 hours at 4° C. Following the incubation period, the solubilized composition was centrifuged at 12,000 rpm for 20 minutes at 4° C. and the insoluble pellet was discarded. The supernatant was dialyzed extensively against 0.01 N HCl at 4° C. in dialysis tubing with a 3500 MWCO (Spectrum Medical Industries). Polymerization of the solubilized extracellular matrix composition was achieved by dialysis against PBS, pH 7.4, at 4° C. for about 48 hours. The polymerized construct was then dialyzed against several changes of water at room temperature and was then lyophilized to dryness.

The polymerized construct had significant mechanical integrity and, upon rehydration, had tissue-like consistency and properties. In one assay, glycerol was added prior to polymerization by dialysis and matrices with increased mechanical integrity and increased fibril length resulted.

Example 10

Preparation of Extracellular Matrix Threads

Small intestinal submucosa was harvested and prepared from freshly euthanized pigs (Delphi Ind.) as previously disclosed in U.S. Pat. No. 4,956,178. Intestinal submucosa was powderized under liquid nitrogen and stored at −80° C. prior to use. Digestion and solubilization of the material was performed by adding 5 grams of powdered tissue to each 100 ml of solution containing 0.1% pepsin in 0.01 N hydrochloric acid and incubating for 72 hours at 4° C. Following the incubation period, the solubilized composition was centrifuged at 12,000 rpm for 20 minutes at 4° C. and the insoluble pellet was discarded.

The solubilized extracellular matrix composition (at 4° C.) was placed in a syringe with a needle and was slowly injected into a PBS solution at 40° C. The solubilized extracellular matrix composition immediately formed a filament with the diameter of the needle. If a blunt-tipped needle is used, straight filaments can be formed while coiled filaments can be formed with a bevel-tipped needle. Such filaments can be used as resorbable sutures.

Example 11

Lyophilization and Reconstitution of Solubilized ECM Compositions

Frozen small intestinal submucosa powder that had been prepared by cryogenic milling was centrifuged at 3000×g for 15 minutes and the excess fluid was decanted. The powder (5% weight/volume) was digested and solubilized in 0.01 N HCl containing 0.1% weight/volume pepsin for approximately 72 hours at 4° C. The solubilized extracellular matrix composition was then centrifuged at 16,000×g for 30 minutes at 4° C. to remove the insoluble material. Aliquots of the solubilized extracellular matrix composition were created and hydrochloric acid (12.1 N) was added to create a range of concentrations from 0.01 to 0.5 N HCl.

Portions of the solubilized extracellular matrix composition were dialyzed (MWCO 3500) extensively against water and 0.01 M acetic acid to determine the effects of these media on the lyophilization product. Aliquots of the solubilized extracellular matrix composition in 0.01 M acetic acid were created and glacial acetic acid (17.4 M) was added to create a range of concentrations from 0.01 to 0.5 M acetic acid. The solubilized extracellular matrix compositions were frozen using a dry ice/ethanol bath and lyophilized to dryness. The lyophilized preparations were observed, weighed, and dissolved at 5 mg/ml in either 0.01 N HCl or water. The dissolution and polymerization properties were then evaluated. The results are shown in Tables 4-8.

TABLE 4

Gross appearance of solubilized extracellular matrix compositions following lyophilization at various hydrochloric acid concentrations.

| [HCl] (N) | Appearance |
| --- | --- |
| 0.01 | Light, fluffy, homogenous, foam-like sheet; white to off-white in color; pliable |
| 0.05 | Slightly wrinkled and contracted, some inhomogeneities in appearance noted, slight brown tint, pliable to slightly friable in consistency |
| 0.10 | Wrinkled, collapsed in appearance; inhomogeneities noted, some regional "melting" noted; significant brown tint; friable |
| 0.25 | Wrinkled, collapsed in appearance; increased inhomogeneities noted, increased areas of regional "melting" noted; significant brown tint; friable |
| 0.50 | Significant collapse and shrinkage of specimen, dark brown coloration throughout; dark brown in color; friable |

TABLE 5

Dissolution properties of solubilized extracellular matrix compositions following lyophilization at various hydrochloric acid concentrations.

| [HCl] (N) Reconstitution Medium | Reconstitution Properties | |
| --- | --- | --- |
| | $H_2O$ | 0.01N HCl |
| 0.01 | Completely dissolved in 20-30 minutes, pH 4 | Completely dissolved in 20-30 minutes, pH 2 |
| 0.05 | Majority dissolved in 2 hours; slight particulate noted, pH 3-4 | Majority dissolved in 40 minutes; very slight particulate noted, pH 2 |
| 0.1 | Incomplete dissolution | Incomplete dissolution |
| 0.25 | Incomplete dissolution | Incomplete dissolution |
| 0.5 | Incomplete dissolution | Incomplete dissolution |

TABLE 6

Polymerization properties of solubilized extracellular matrix compositions following lyophilization at various hydrochloric acid concentrations.

| [HCl] (N) Reconstitution Medium | Polymerization Properties | |
| --- | --- | --- |
| | $H_2O$ | 0.01N HCl |
| 0.01 | Polymerized within 20-30 minutes | Polymerized within 10-20 minutes |
| 0.05 | Weak gel noted at 45 minutes; significant lag time in gelling | Polymerized within 20-30 minutes |
| 0.1 | *No Polymerization | *No Polymerization |
| 0.25 | *No Polymerization | *No Polymerization |
| 0.5 | *No Polymerization | *No Polymerization |

TABLE 7

Dissolution properties of solubilized extracellular matrix compositions following lyophilization at various acetic acid concentrations.

| [Acetic Acid] (M) | Reconstitution Properties | |
| --- | --- | --- |
| | Reconstitution in $H_2O$ | Reconstitution in 0.01N HCl |
| 0.01 | Completely dissolved in 90 minutes, pH 5 | Completely dissolved in 90 minutes, pH 1-2 |
| 0.05 | Near complete dissolution after 90 minutes; small particulate remained, pH 5 | Completely dissolved in 90 minutes, pH 1-2 |
| 0.1 | Completely dissolved in 90 minutes, pH 5 | Near complete dissolution in 90 minutes; small particulate, pH 1-2 |
| 0.25 | Completely dissolved in 90 minutes, pH 5 | Completely dissolved in 90 minutes, pH 1-2 |
| 0.5 | Near complete dissolution after 90 minutes; small particulate remained, pH 5 | Completely dissolved in 90 minutes, pH 1-2 |

TABLE 8

Polymerization properties of solubilized extracellular matrix compositions following lyophilization at various acetic acid concentrations.

| [Acetic Acid] (M) Reconstitution Medium | Polymerization Properties | |
|---|---|---|
| | H₂O | 0.01N HCl |
| 0.01 | Polymerized within 5 | 10 minutes |
| 0.05 | Polymerized within 5 | 10 minutes |
| 0.1 | Polymerized within 5 | 10 minutes |
| 0.25 | Polymerized within 5 | 10 minutes |
| 0.5 | Polymerized within 5 | 10 minutes |

These results show that lyophilization in HCl and reconstitution of solubilized extracellular matrix compositions in 0.01 N HCl to 0.05 N HCl or in water maintains the capacity of the components of the compositions to polymerize. The results also show that lyophilization in acetic acid maintains the capacity of the components of the compositions to polymerize when the composition is polymerized in water or HCl. The solubility rate is lyophilization from 0.01 N HCl>lyophilization from 0.01 M acetic acid≥lyophilization from water.

Example 12

Preparation of Solubilized Submucosa Composition

1. Dissolution: of small intestinal submucosa (SIS) powder in acetic acid with pepsin
    1.1. Preparation of acetic acid with pepsin
        1.1.1. Prepare the desired volume of 0.5 M acetic acid (typically 1 L; this requires 28.7 mL of 17.4 M glacial acetic acid).
        1.1.2. Add the desired mass of pepsin to achieve a 0.1% w/v solution (typically 1 g, if 1 L of acetic acid is used).
        1.1.3. Place the jar containing acetic acid and pepsin on a stir plate and begin mixing.
    1.2. Preparation of centrifuged SIS powder
        1.2.1. Place SIS powder in 50 mL centrifuge tubes.
        1.2.2. Centrifuge SIS powder at 3000×g for 15 minutes.
        1.2.3. Open centrifuge tubes, pour off and dispose of supernate.
        1.2.4. Remove pellets from tubes. Measure out the desired mass to achieve a 5% w/v solution (typically 50 g, if 1 L of acetic acid was used). Previously prepared and frozen material may be used, and excess centrifuged material may be frozen for later use.
    1.3. Add centrifuged SIS pellet material to acetic acid/pepsin solution.
    1.4. Cover and allow it to stir for 72 hours at 4° C.
2. Centrifugation of dissolved SIS
    2.1. When removed from stirring, the SIS/pepsin solution should appear viscous and somewhat uniform. Pour SIS/pepsin solution into centrifuge jars. Balance jars as necessary.
    2.2. This mixture should be centrifuged at 16,000×g for 30 minutes at 4° C. Refer to the operators manual or SOP for instructions on using the centrifuge. If using the Beckman model J2-21, use the JlO head at a speed of 9500 rpm.
    2.3. Remove jars of SIS from centrifuge. Pour the supernatant into a clean jar. Be careful not to disturb the pellet, and stop pouring if the SIS begins to appear more white and creamy (this is pellet material).
3. Dialysis of SIS in water and hydrochloric acid
    3.1. Prepare dialysis tubing as follows:
        3.1.1. Use dialysis tubing with MWCO 3500, diameter 29 1mll. Handle dialysis tubing with gloves, and take care not to allow it to contact foreign surfaces, as it may easily be damaged.
        3.1.2. Cut dialysis tubing to the necessary length. (typically, 3 sections of about 45 cm).
        3.1.3. Wet tubing in millipore water, and leave tubing in the water until each piece is needed.
        3.1.4. Do the following with each length of tubing:
            3.1.4.1. Place a clip near one end of the tubing.
            3.1.4.2. Holding the tubing to avoid contact with foreign surfaces, use a pipette to fill the tubing with SIS solution. Each piece of tubing should receive roughly the same volume of SIS (for example, if three lengths of tubing are used, measure one third of the total volume into each).
            3.1.4.3. Place a clip on the open end of the dialysis tubing. Avoid leaving slack. The tube should be full and taut.
            3.1.4.4. Place the filled dialysis tubing in a container of 0.01 M HCL with a stir bar.
            3.1.4.5. Repeat the above steps to fill all lengths of tubing.
        3.1.5. Leave containers to stir at 4o C.
    3.2. Details regarding changing the dialysis in 0.01 M HCl are given below.
        3.2.1. The 0.01 M HCl in the dialysis containers must be changed several times. This should be done as follows:
        3.2.2. After changing the 0.01 M HCl, another change should not be done for at least two hours.
        3.2.3. Change the 0.01 M HCl at least 10 times, over a period of at least four days. This assumes a ratio of 200 mL SIS to 6 L of 0.01 M HCl. If a higher ratio is used, more changes may be necessary.
        3.2.4. When changing 0.01 M HCl, do not leave dialysis bags exposed in the air or on the counter. Use tongs or forceps to move a dialysis bag directly from one container to another. (It is okay to have multiple dialysis bags in one container.) Dump the first container in the sink, then refill it with millipore water. The dialysis bags can now be placed in the newly filled container while the other container or containers are changed.
4. Sterilization of SIS
    4.1. Place dialysis bags of SIS in a solution of 0.18% Peracetic acid/4.8% Ethanol. Leave to stir for two hours (more time may be necessary).
    4.2. Translocate dialysis bags to 0.01 M HCl, and continue dialysis as before.
    Continue for at least 2 days, changing HCl at least 3 times daily.
    4.3. When dialysis is complete, dialysis tubing filled with SIS should be removed from the HCl.
    4.4. Remove the clips. Cut open one end of the dialysis tubing and pour SIS into a clean jar.
    4.5. SIS should be refrigerated until use.
5. Lyophilization of SIS
    5.1. Operating the Vertis Freezemobile
        5.1.1. Make sure the condenser is free of any water. (The condenser is the metal cylinder which opens on the front of the lyophilizer.) Ensure that the black rubber collection tubing attached to the bottom of the condenser is plugged. This can be accessed by opening the grate on the front of the lyophilizer.
- 5.1.2. Close the door of the condenser, the top of the manifold, and all sample ports. If the door of the condenser or the top of the manifold are not forming a good seal, apply a small amount of vacuum grease to the rubber contact surfaces.
- 5.1.3. Turn on the "Refrigerate" switch. The indicator on the front of the lyophilizer will show a light beside "Condenser" and beneath "On." The light beneath "OK" will not illuminate until the condenser is cooled. The condenser temperature is indicated when the digital readout displays "C1."
- 5.1.4. When the "condenser" indicator light under "OK" is illuminated, on the "Vacuum" switch. The indicator will show a light beside "Condenser" and beneath "On." The light beneath "OK" will not turn on until the chamber is sufficiently evacuated. The chamber pressure is indicated when the digital readout displays "V 1."
- 5.1.5. The rollers can be used for freezing a coat of material on the inside surface of a jar. To use the rollers, first ensure that the drain tube is plugged. (This can be accessed through the door on the right side of the front of the lyophilizer.) Using 100% Ethanol, fill the roller tank to a level several millimeters above the top of the rollers. Under-filling will cause ineffective cooling while over-filling will allow ethanol to leak into the jars. The temperature of ethanol bath is indicated when the digital readout displays "T1." This bath is cooled when the "Refrigerate" switch is turned on. The "Rollers" switch controls the turning of the rollers, and may be switched off when no jar is on the rollers.

5.2. Lyophilizing SIS
- 5.2.1. Lyophilization jars, glass lids, and rubber gaskets should be cleaned with ethanol. Allow ethanol to evaporate completely before use. Mid-size jars, lids, and gaskets (3-inch diameter) should be used to fit into the roller if using the Virtis Freezemobile Jar lyophilization.
- 5.2.2. Pipette 75 mL of SIS solution into the lyophilization jar. Place gasket and lid on jar.
- 5.2.3. Seal the jar by covering the openings with parafilm. Note the small hole on the neck of the lid, which must be covered.
- 5.2.4. Place the jar of SIS on the lyophilizer rollers for a minimum of 2 hours.
- 5.2.5. Alternatively, the jar may be placed in a freezer until all material is solid. In a −80° C. freezer, this takes about 30 minutes.
- 5.2.6. Prepare a spigot on the lyophilizer by inserting a glass cock with the tapered end out. The tapered end of the cock should be coated with vacuum grease.
- 5.2.7. Remove the jar of SIS from the rollers (or freezer). Place springs on the hooks to hold the jar and lid together. Remove the parafilm and place the neck of the lid of the jar over the cock. Rotate the jar so that the holes in the lid and the cock do not align. The spigot can be rotated so that the jar rests on the top surface of the lyophilizer.
- 5.2.8. Turn the valve switch so that it points toward the jar of S1S.
- 5.2.9. More jars may be added to freeze-dry simultaneously, but add jars one or two at a time. Wait until the vacuum pressure falls to a reasonable range (e.g. 200 millitorr) to ensure that the last jar is sealed before adding subsequent jars.
- 5.2.10. Leave the jars under vacuum for at least 24 hours.
- 5.2.11. After lyophilization is complete, turn the switch On the spigot to point away from the jar. This will allow air into the jar.
- 5.2.12. Remove the jar from the cock.
- 5.2.13. Lyophilized material is not immediately used, it should be stored in a dry environment. Use a large, sealable container with Dri-Rite or another desiccant, and place containers of lyophilized material therein.

6. Rehydration of lyophilized SIS 6.1. Place lyophilized SIS into a tube or jar.

6.2. Add the desired quantity of liquid (typically 0.01 N HCl) to the container of SIS.

6.3. Mixing may be accelerated by shaking, stirring, etc. Store container under refrigeration until dissolution of SIS is complete.

Sterilization of Solubilized SIS by Dialysis Against Peracetic Acid Containing Solution 1. Dialyze solubilized SIS against a large reservoir containing 0.18% peracetic acid/4.8% ethanol in water. Dialysis time may vary depending upon peracetic acid concentration, dialysis membrane molecular weight cut off, temperature, etc.

2. Transfer dialysis bags aseptically to reservoirs containing 0.01 N HCl. Dialyze extensively to reduce concentration of residual peracetic acid.

3. When dialysis is complete, dialysis tubing filled with solubilized SIS should be removed from the dialysis tank aseptically.

4. Remove dialysis clips and pour or pipette solubilized SIS into a sterile jar.

5. The disinfected solubilized SIS should be stored at 4° C. until use.

Sterilization of SIS by Direct Addition of Peracetic Acid to SIS Solution

1. Add 100% Ethanol and 32 wt % peracetic acid to solubilized SIS to create a solution with final concentration of 0.18% peracetic acid/4.8% ethanol. Stir well and leave for two hours.

2. Place solubilized SIS in aseptic dialysis bags. Dialyze against sterile solution of 0.01 N HCl.

3. When dialysis is complete, dialysis tubing filled with solubilized SIS should be removed from the dialysis tank aseptically.

4. Remove dialysis clips and pour or pipette solubilized SIS into a sterile jar.

5. The disinfected solubilized SIS should be stored at 4° C. until use.

While the invention has been illustrated and described in full detail in the drawings and foregoing description, the same is to be considered as illustrative and not restrictive in character, it being understood that only the preferred embodiment has been shown and described and that all changes and modifications that come within the spirit of the invention are desired to be protected. In addition, all publications cited in this application are indicative of the abilities possessed by those of ordinary skill in the pertinent art and are hereby incorporated by reference in their entirety as if each had been individually incorporated by reference and fully set forth. U.S. patent application Ser. No. 11/435,393 filed May 16, 2006, entitled "Engineered Extracellular Matrices", naming as inventor Sherry L. Yoytik-Harbin, is also hereby incorporated herein by reference in its entirety.

What is claimed is:

1. An extracellular matrix composition, comprising:
a dry collagenous powder comprising an extracellular matrix hydrolysate material, wherein said extracellular matrix hydrolysate material is effective to gel upon rehydration with an aqueous medium, and wherein said extracellular matrix hydrolysate material has been formed by digesting an extracellular matrix material with a hydrochloric acid solution containing an enzyme that digests the extracellular matrix material.

2. The composition of claim 1, wherein the extracellular matrix hydrolysate material comprises components from vertebrate submucosa tissue.

3. The composition of claim 1, wherein the extracellular matrix hydrolysate material has been prepared by a process comprising solubilizing an extracellular matrix composition with hydrochloric acid to produce a solubilized extracellular matrix material, and lyophilizing the solubilized extracellular matrix material to produce a lyophilized, solubilized extracellular matrix material that is capable of polymerizing upon rehydration.

4. A method of preparing a lyophilized extracellular matrix composition, comprising the steps of:
solubilizing an extracellular matrix composition with a hydrochloric acid solution containing an enzyme that digests the extracellular matrix composition to produce a solubilized extracellular matrix composition; and
lyophilizing the solubilized extracellular matrix composition from a solution having a pH of about 6 or below to produce a lyophilized, solubilized extracellular matrix composition.

5. The method of claim 4, wherein the extracellular matrix composition that is solubilized comprises vertebrate submucosa tissue or basement membrane tissue.

6. An extracellular matrix composition prepared by a process comprising:
solubilizing an extracellular matrix composition with a hydrochloric acid solution containing an enzyme that digests the extracellular matrix composition, to form a solubilized composition of extracellular matrix components; and
lyophilizing the solubilized composition from a hydrochloric acid solution to produce a lyophilized, solubilized extracellular matrix composition wherein the lyophilized, solubilized composition, when dissolved at a concentration of 5 mg/ml in a 0.01 M hydrochloric acid solution, is capable of polymerization within 30 minutes.

7. The composition of claim 6, wherein the enzyme is pepsin.

8. The composition of claim 6, wherein the hydrochloric acid solution containing an enzyme that digests the extracellular matrix composition is a 0.01 M to 0.05 M hydrochloric acid solution containing an enzyme that digests the extracellular matrix composition.

9. The method of claim 4, wherein said lyophilizing is conducted in the absence of acetic acid.

10. The method of claim 4, wherein said enzyme is pepsin.

11. The method of claim 8, wherein the hydrochloric acid is at a concentration of about 0.01 M.

12. A composition comprising a lyophilized extracellular matrix hydrolysate and an acid excipient comprising hydrochloric acid, wherein the lyophilized extracellular hydrolysate, when dissolved at a concentration of 5 mg/ml in a 0.01 M hydrochloric acid solution, is capable of polymerization within 30 minutes.

13. The composition of claim 12 wherein the lyophilized extracellular matrix hydrolysate is prepared by lyophilizing the extracellular matrix hydrolysate from a 0.01 M to 0.05 M hydrochloric acid solution.

14. The composition of claim 13, wherein the lyophilized extracellular matrix hydrolysate is prepared by lyophilizing the extracellular matrix hydrolysate from an about 0.01 M hydrochloric acid solution.

* * * * *